United States Patent [19]

Cox

[11] Patent Number: 4,859,712

[45] Date of Patent: Aug. 22, 1989

[54] SILICONE FOAM AND METHOD FOR MAKING IT

[75] Inventor: James E. Cox, Oxnard, Calif.

[73] Assignee: Cox-Uphoff International, Carpinteria, Calif.

[21] Appl. No.: 256,648

[22] Filed: Oct. 12, 1988

[51] Int. Cl.⁴ .............................................. C08J 9/26
[52] U.S. Cl. ...................................... 521/62; 521/154
[58] Field of Search ................................... 521/61, 154

[56] References Cited

U.S. PATENT DOCUMENTS 4,157,424  6/1979  Boutle ................................... 521/61
4,242,464 12/1980  Boutle ................................... 521/61
4,405,360  9/1983  Cardarelli ............................. 521/92

Primary Examiner—Morton Foelak
Attorney, Agent, or Firm—Donald D. Mon

[57] ABSTRACT

A method to make a silicone foam. A layer of crystalline material is embedded in a layer of uncured silicone. The crystalline material is closely packed in crystal-to-crystal contact, the crystals being provided in a plurality of sizes or ranges of size to increase the packing ratio of the crystals as a group. The silicone is cured and then the crystals are dissolved out with a solvent that dissolves them but does not dissolve the silicone.

2 Claims, 1 Drawing Sheet

SILICONE FOAM AND METHOD FOR MAKING IT

FIELD OF THE INVENTION

This invention relates to the manufacture of a silicone foam, and especially to such a foam which is useful for the surface of implants for implantation in the human body.

BACKGROUND OF THE INVENTION

Prostheses for implantation in the human body have a substantial size and shape intended to augment or replace body tissues. Because they do not react unfavorably with human tissue, medical grade silicones are the preferred material of construction. Generally a prosthesis has an envelope which holds a deformable material which with the envelope simulates the properties of the tissue that it replaces or augments. Known such materials are silicone gels, and normal saline solution. Obviously the envelope material must be impervious or at least only semi-permeable to what it contains so it does not readily leach or leak into the body. It is general practice for these envelopes to have a smooth outer surface.

There is a growing body of belief to the effect that smooth envelope surfaces have the tendency to become encapsulated in a hard encapsulation developed by the body when it recognizes the implant as a foreign body. Especially in the field of mammary implants, these spherical encapsulations can become individual bodies that are separately palpable, and are quite hard. This totally frustrates the intended purpose of the prosthesis, and quite frequently requires a revision of the procedure. This revision means the implantation of another prosthesis. In such a situation, everybody loses. The patient is distressed and subjected to the risks and expenses of a second procedure, and the surgeon is subjected to attendant risks and client displeasure.

A line of prostheses has been developed which is covered by a material with a roughened surface. This surface has a wealth of cavities and fibrous structures. It is generally an open cell foam, cleanly cut to make this surface texture. The material used for this purpose is usually a urethane open cell foam. It would be preferred to use a silicone foam for this purpose, but known efforts to provide silicone foams have not provided a foam structure which the inventor herein regards as suitable. The terms "foam" and "sponge" are used interchangeably herein to denote an open cell construction wherein cavities in the material interconnect with one another.

It is an object of this invention to provide a silicone foam and a method to make it, and especially to form it on the surface of a continuous substrate so the resulting construction has an inherent and continuous outer roughened surface region, and an interior layer which is impervious or at least only semi-permeable, to what it must contain.

It is unimportant to the invention that the cellular construction extend all the way through the material, but this is possible to make if only a foam is desired. However in the field of implants it is the surface configuration with cavities and fibrous material which is important to surrounding tissue. A depth of perhaps no more than about 1 millimeter of such texture, is of consequence. Much deeper cellular construction can itself lead to problems of tissue growth.

The inventor herein has found that by embedding soluble crystals in the silicone to a desired depth to which the foam will be produced, curing the silicone, and then dissolving the crystals, an open-foam cell can be made which provides the roughened surface desired for limited tissue ingrowth. The foam can be formed as a surface on an integral and continuous silicon substrate, the depth of the foam being controllable by controlling the depth to which the crystals extend.

The inventor has further found that the use of crystals all of substantially the same size results in a relatively less useful foam. This is because particles of equal size pack together to form a matrix of relatively low percentage of volume ("packing ratio"). If more than one size is used, then a less dense foam can be made, because more crystals can be packed into a given volume. Furthermore, when dissolved out, there is likely to be a greater number of tendrils and interconnecting open cavities, which provides a correspondingly more effective roughened surface.

It is an object of this invention to provide a silicone foam, a silicone body surfaced with an integral silicone foam, and a method for making them.

BRIEF DESCRIPTION OF THE INVENTION

A silicone foam is manufactured by incorporating soluble crystals in uncured silicone, then curing the silicone, and thereafter dissolving out the crystals. The crystals are insoluble in the silicone, and are soluble in a solvent which does not dissolve the cured silicone. The preferred crystal is sodium chloride, because even if it is not totally removed, it does no harm in the human body. The preferred solvent is water.

According to a feature of this invention, a plurality of crystal sizes or size ranges is used in order to improve the packing ratio, and thereby to increase the roughness of the surface after the crystals are dissolved out.

According to a preferred but optional feature of the invention, the crystals are not embedded throughout the entire depth of the silicone, and there results a solid silicone substrate suitable for a fluid or gel containing envelope, with a surfacing on one side having the described roughness.

The above and other features of the invention will be fully understood from the following detailed description and the accompanying drawings, in which:

DETAILED DESCRIPTION OF THE INVENTION

Figure 1:
FIG. 1 is a cross-section of a layer of uncured silicone.

FIG. 1 shows a layer 10 of uncured silicone elastomer, such as room-temperature vulcanizing (RTV) medical grade silicone. It has a lower surface 11 created by applying the monomer to a supporting surface, and an upper surface 12 which is self-leveling while in the fluid state.

Figure 2:
FIG. 2 is a somewhat schematic showing of a fragment of the sheet of FIG. 1 with crystals embedded in its upper surface.
Figure 3:
FIG. 3 is a somewhat schematic cross-section showing of a fragment of the sheet of FIG. 3, having been cured and with the crystals dissolved out.

FIG. 2 shows that a quantity of crystals 15 has been pressed into upper surface 12, to a depth 13. The crystals become embedded in the silicone, and as will later be disclosed, are in contact with one another. As a group they are embraced by the liquid silicone.

Should a layer completely of foam be desired, the crystals will have been pressed all the way through the monomer from surface to surface. However, the unsupported foam will rarely be strong enough to endure substantial handling. Therefore in the embodiment preferred for implants, a depth 16 of silicone remains without the crystals. The structure of FIG. 2 is cured, and becomes a flexible elastomeric body with crystals in its upper region.

After the body is cured, the crystals are dissolved out of it, leaving voids where they were when the layer was cured. It is practically impossible accurately to illustrate the resulting structure, but the voids will be open-cellular, where the crystals were, and where they were in contact with one another. The remaining elastomer will be a construction with many cavities, tendrils, walls, and fragments of walls. For convenience, this type of surface is sometimes called a "roughened surface".

Figure 4:
FIG. 4 is a somewhat schematic top view taken at line 4—4 in FIG. 3.

FIG. 4 attempts to show that there are many openings into the foam layer 17. The foam layer, having been formed as the consequence of being cured as a continuous structure with the underlying impermeable substrate layer 18, is integral with it and supported by it. As a consequence there results a structurally sound and easily handled silicone foam-faced material of construction. The material can be shaped as desired. If preferred, this process can be carried out on a layer being formed on a mandrel or on some other device so that when completed it already has a desired shape with little or no cutting or cementing required.

Any suitable curable liquid silicone can be used for this product. The details of processing the material are well-known in the silicone art and require no description here. The cured material is usually semi-permeable, but its permeability is not so great as to preclude its usage satisfactorily to contain silicone gels or normal salines for long periods of time. Some silicones may be totally impermeable, but are not in general usage in mammary implants. They are also suitable for use with this invention.

It is best practice to use crystalline material, because the irregularity of the crystals provide increased roughness within the cells, and because the likelihood of contact with adjacent crystals is greater than if, for example, a spherical product were used instead.

The preferred crystal is sodium chloride. Any other compound which is insoluble in the silicone, soluble in a solvent that does not dissolve the silicone, and which as a residue is harmless to the body, could be used instead.

Water is the preferred solvent. Any other solvent which dissolves the crystals and not the silicone, and which leaves no deleterious residue, could be used instead.

The properties of this foam will be improved, for the reasons stated above, by using a plurality of crystal sizes. Of course crystal sizes are never truly uniform, and are generally defined by percentages retained on standard screens. Two useful sizes, mixed in about equal proportions, are sodium chloride salt sold by Morton Salt division of Morton Thiokol, Inc. of Chicago; Ill.

One is table salt, predominantly retained on United States Standard Meshes between 30 and 50 mesh.

The other is KD Fine Solar Salt, predominantly retained on United States Standard Meshes between about 16 and 40 mesh.

When well mixed and embedded as shown, a very satisfactory silicone foam can be made.

More than two size ranges could be used, or more narrow and specific ranges could be provided for each. However, the use of only the two sizes and ranges as shown have proved to be fully satisfactory.

This invention is not to be limited by the embodiments shown in the drawings and described in the description, which are given by way of example and not of limitation, but only in accordance with the scope of the appended claims.

I claim:

1. The method of preparing a silicone foam comprising embedding in a layer of uncured silicone a layer of crystalline material, the crystalline material being closely packed and generally in crystal-to-crystal contact, and embraced by the liquid silicone, curing the silicone, and with a solvent which dissolves the crystals but does not dissolve the cured silicone dissolving out the crystals, the crystals being provided in a plurality of sizes or ranges of sizes to increase the packing ratio of the crystals as a group whereby to produce a structure of said cured silicone having a great number of tendrils and intercommunicating cavities.

2. The method of claim 1 in which the crystals are sodium chloride, and the solvent is water.

* * * * *